United States Patent
Allard et al.

(10) Patent No.: US 6,399,048 B1
(45) Date of Patent: *Jun. 4, 2002

(54) SELF-TANNING COSMETIC COMPOSITIONS

(75) Inventors: Delphine Allard, Colombes; Serge Forestier, Claye Souilly, both of (FR)

(73) Assignee: L'Oreal, Paris (FR)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 21 days.

(21) Appl. No.: 09/053,822

(22) Filed: Apr. 2, 1998

(30) Foreign Application Priority Data

Apr. 4, 1997 (FR) .......................................... 97 04159

(51) Int. Cl.⁷ .............................................. A61K 7/021
(52) U.S. Cl. ................................. 424/63; 424/DIG. 16
(58) Field of Search ........................... 424/DIG. 16, 63

(56) References Cited

U.S. PATENT DOCUMENTS

| | | | |
|---|---|---|---|
| 4,289,872 A | 9/1981 | Denkewalter et al. | 528/328 |
| 4,360,646 A | 11/1982 | Denkewalter et al. | 525/420 |
| 4,507,466 A | 3/1985 | Tomalia et al. | 528/332 |
| 4,558,120 A | 12/1985 | Tomalia et al. | 528/363 |
| 4,568,737 A | 2/1986 | Tomalia et al. | 528/332 |
| 4,587,329 A | 5/1986 | Tomalia et al. | 528/363 |
| 4,631,337 A | 12/1986 | Tomalia et al. | 528/391 |
| 4,694,064 A | 9/1987 | Tomalia et al. | 528/332 |
| 5,302,378 A | * 4/1994 | Crotty et al. | 424/59 |
| 5,788,989 A | 8/1998 | Jansen et al. | 424/486 |
| 5,834,513 A | * 11/1998 | Ptchelintsev et al. | |

FOREIGN PATENT DOCUMENTS

| | | |
|---|---|---|
| EP | 0 234 408 | 9/1987 |
| EP | 0 671 159 | 9/1995 |
| EP | 0 684 044 | 11/1995 |
| FR | 2 586 913 | 3/1987 |
| WO | WO 93/14147 | 7/1993 |
| WO | WO 94/04130 | 3/1994 |
| WO | WO 94/13258 | 6/1994 |
| WO | WO 94/22419 | 10/1994 |
| WO | WO 95/02008 | 1/1995 |
| WO | WO 95/15742 | 6/1995 |
| WO | WO 95/26179 | 10/1995 |
| WO | WO 97/33560 | 9/1997 |

OTHER PUBLICATIONS

G.R. Newkome et al., "Dendritic Molecules," Table of Contents only.

Donald A. Tomalia et al., "Starburst Dendrimers: Molecular-Level Control of Size, Shape, Surface Chemistry, Topology, and Flexibility from Atoms to Macroscopic Matter," *Angewandte Chemie*, vol. 29, No. 2, pp. 138–175 (Feb. 1990).

Nicole Ardoin et al., "Molecular trees: from syntheses towards applications," *Bulletin de la Societe Chimique de France*, pp. 875–909 (1995) vol. 132.

B. I. Voit, "Dendritic polymers: from aesthetic macromolecules to commercially interesting materials," *Acta 2/'95 Polymerica*, vol. 46, No. 2, pp. 87–99 (Apr. 1995).

Craig J. Hawker et al., "Preparation of Polymers with Controlled Molecular Architecture. A New Convergent Approach to Dendritic Macromolecules," *Journal of the American Chemical Society*, vol. 112, No. 21, pp. 7638–7647 (Oct. 1990).

* cited by examiner

*Primary Examiner*—Diana Dudash
*Assistant Examiner*—Alysia Berman
(74) *Attorney, Agent, or Firm*—Finnegan, Henderson, Farabow, Garrett, and Dunner, L.L.P.

(57) ABSTRACT

Novel cosmetic compositions for artificially tanning the skin, comprising at least one self-tanning agent, in particular DHA, and at least one dendrimer.

16 Claims, No Drawings

SELF-TANNING COSMETIC COMPOSITIONS

The present invention relates to novel cosmetic compositions for topical use intended more particularly for artificially tanning and/or browning the skin (compositions referred to hereinbelow more simply as self-tanning compositions), as well as to their use in the abovementioned cosmetic application. Even more precisely, the invention relates to self-tanning compositions comprising at least one self-tanning agent, preferably dihydroxyacetone, and at least one polymer selected from dendrimers, preferably a dendrimer containing amine functions.

It is known that dihydroxyacetone, or DHA, is a particularly advantageous product which is commonly used in cosmetics as an agent for artificially tanning the skin; when applied to the skin, especially the face, it allows a tanning or browning effect to be obtained which is similar in appearance to that which can result from prolonged exposure to the sun (natural tanning) or to a UV lamp. Such a use also has the advantage of entirely avoiding the risks of skin reaction generally associated with the abovementioned prolonged exposures (erythema, burns, loss of elasticity, appearance of wrinkles, premature ageing of the skin, and the like).

Most of the cosmetic products intended for artificially tanning the skin use dihydroxyacetone (DHA) as active agent, but its use is not entirely satisfactory.

The reason for this is that the reaction of DHA with the amino acids in the skin is not immediate and the skin coloration does not appear until a few hours (about 3 hours) after the application. In addition, the skin coloration imparted by DHA is not particularly natural since it is an orange-yellow shade.

Various solutions have been recommended in order to obtain with DHA a faster coloration and a shade which is closer to that of a natural tan.

In particular, combinations of DHA with amine compounds are described in several documents.

Patent applications WO 95/26179 and WO 94/22419 describe the combination of DHA with amino acids.

Patent application WO 94/04130 describes the combination of DHA with primary amines.

Patents WO 94/13258 and WO 95/15742 describe the combination of DHA with a polyamine compound, it being possible for the polyamine to be, for example, polyethyleneimine (hyperbranched polymer) or an aminosilicone.

These combinations make it possible to obtain a faster rise in the coloration than with DHA alone, but improvement is still sought in terms of shade of coloration (orange-yellow), fastness of the coloration, in particular its fastness to washing, and the intensity of the coloration.

The aim of the present invention is, in particular, to solve the above problems by proposing novel self-tanning combinations, in particular DHA-based combinations which are of improved efficacy and/or self-tanning activity on the skin: speed of coloration, quality of the coloration, intensity and fastness.

The inventors have observed, surprisingly, that the combination of a self-tanning active agent, in particular dihydroxyacetone or DHA, with a dendrimer can make it possible to obtain an artificial coloration of the skin which is faster than with DHA alone and faster than the other combinations of DHA with amine compounds according to the prior art. It also can allow a shade closer to that of a natural tan to be obtained. In addition, such a combination gives the tan a very satisfactory intensity and very good fastness over time, in particular good resistance to washing.

A subject of the invention is the combination of at least one self-tanning active agent and at least one polymer selected from dendrimers. More particularly, the self-tanning active agent is dihydroxyacetone.

Another subject of the invention is cosmetic compositions intended for topical application, comprising such a combination.

The invention also relates to devices or kits containing at least two compartments, each of the compartments containing one of the components of the combination defined above.

Other subjects of the invention will become apparent on reading the description and the examples which follow.

The self-tanning active agent can preferably be selected from: mono- or polycarbonyl derivatives, such as DHA, isatin, alloxane, ninhydrin, glyceraldehyde, mesotartaric aldehyde and pyrazoline-4,5-dione derivatives. The self-tanning active agent more preferably used in the present invention is dihydroxyacetone.

These self-tanning active agents can optionally be combined with direct dyes or with indole derivatives.

Hyperbranched polymers, a category of polymer to which polyethyleneimine belongs, are molecular constructions having a branched structure, generally around a core. Their structure generally lacks symmetry: the base units or monomers used in the construction of the hyperbranched polymer can be of different natures and they are distributed irregularly. The branches of the polymer can be of different natures and lengths. The number of base units, or monomers, can be different depending on the different branching.

Hyperbranched polymers are generally derived from the polycondensation of one or more monomers ABx, A and B being reactants capable of reacting together, x being an integer greater than or equal to 2, but other preparation processes can be envisaged. Hyperbranched polymers are characterized by their degree of polymerization DP=1–b, b being the percentage of non-terminal functionalities in B which have not reacted with a group A. Since the condensation is non-systematic, in contrast with the synthesis of dendrimers, the degree of polymerization is less than 100%. Usually, by the known synthetic methods, the DP ranges from 15 to 90%.

Dendrimers are highly branched polymers and oligomers that are also known per se, having a well-defined chemical structure, and they are said to be "perfect" hyperbranched polymers. In general, dendrimers comprise a core, a defined number of generations of branches, or spindles, and terminal groups. The generations of spindles comprise structural units, which are identical for the same generation of spindles and which can be identical or different for different generations of spindles. The generations of spindles extend radially in a geometrical progression from the core. The terminal groups of a dendrimer of the Nth generation are the terminal functional groups of the spindles of the Nth generation or terminal generation. Such polymers are described in particular in D. A. Tomalia, A. M. Naylor and W. A. Goddard III, Angewandte Chemie, Int. Ed. Engl. 29, 138–175(1990); C. J. Hawker and J. M. J. Frechet, J. Am. Chem. Soc., 112, 7638(1990); B. I. Voit, Acta Polymer., 46, 87–99 (1995); N. Ardoin and D. Astruc, Bull. Soc. Chim. Fr. 132, 875–909 (1995); G. R. Newkome, C. N. Moorefield, F. Vögtle, Dendritic Molecules, VCH Verlagsgesellschaft, 1996, the disclosures of which are specifically incorporated by reference herein.

Dendrimers can also be defined more particularly by the formula (DI) below:

$$C[A_1B_1(A_2B_2(\ldots(A_{n-1}B_{n-1}(A_nB_n(T)r_n)r_{n-1})r_{n-2}\ldots)r_2)r_1]s \quad (DI)$$

in which:
C represents the core, connected via a number s of functionalities to s spindles $A_1B_1$ via groups $A_1$;
s is an integer greater than or equal to 1 and less than or equal to the number of functionalities in C;
for each spindle $(A_iB_i)$ (i=1, 2 . . . n), the group $B_i$ is connected to $r_i$ groups $A_{i+1}$ of a spindle $(A_{i+1}B_{i+1})$;
each group $A_i(i≧2)$ is connected to only one group $B_{i-1}$ of the spindle $A_{i-1}B_{i-1}$);
$r_i$(i=1, 2 . . . n−1) represents the number of functionalities in the group $B_1$ belonging to the spindle $(A_1B_1)$, $r_i$ being an integer greater than or equal to 2;
the index i (i=1, 2 . . . n) is an integer which denotes the generation of each spindle;
the spindle of the nth generation $A_nB_n$ is chemically linked to a number $r_n$ of terminal groups T, $r_n$ being an integer greater than or equal to zero.

The definition of dendrimers given above includes molecules with symmetrical branching; it also includes molecules with non-symmetrical branching such as, for example, dendrimers in which the spindles are lysine groups, in which the branching of one generation of spindles on the previous generation takes place on the α and ε amines of lysine, which leads to a difference in the length of the spindles for the different branching.

Dense star polymers, starburst polymers and rod-shaped dendrimers are included in the present definition of dendrimers. The molecules known as arborols and cascade molecules also come within the definition of dendrimers according to the present invention.

Several dendrimers can be combined together, via a covalent bond or another type of bonding, by means of their terminal groups, to give species known as "bridged dendrimers" or "dendrimer aggregates". Such species are included in the definition of dendrimers according to the present invention.

Dendrimers can be in the form of an assembly of molecules of the same generation, which are so-called monodispersed assemblies; they can also be in the form of assemblies of different generations, which are so-called polydispersed assemblies. The definition of dendrimers according to the present invention includes monodispersed assemblies and polydispersed assemblies of dendrimers.

The invention relates more particularly to dendrimers containing amine terminal groups.

Preferably, in particular for solubility reasons, their terminal groups bear a primary amine function.

Reference can be made to the following documents in which dendrimers are described in which the terminal group contains an amine function, the content of these documents being specifically incorporated by reference into the present description: U.S. Pat. No. 4,694,064; U.S. Pat. No. 4,507,466; U.S. Pat. No. 4,631,337; U.S. Pat. No. 4,558,120; U.S. Pat. No. 4,568,737; U.S. Pat. No. 4,587,329; WO-A-9502008; WO-A-9314147; EP-234,408; U.S. Pat. No. 4,289,872; U.S. Pat. No. 4,360,646; Proc. Natl. Acad. Sci. USA, 85, 5409–5413 (1988); WO 95/02008; WO 93/14147.

The dendrimers containing amine terminal groups are, for example, polyamidoamines, for example such as those sold under the brand name STARBURST PAMAM by the company Dendritech (block copolymers of ethylenediamine and of methyl acrylate). They can also be selected from dendrimers of the polyalkylamine type, for example such as the polyethyleneimines and polypropyleneimines manufactured by the company DSM.

Dendrimers containing amine terminal groups can also comprise a core and generations of base units, monomers or spindles of any nature, on which a terminal group T bearing an amine function has been grafted.

Preferably, the dendrimers used according to the present invention contain base units (monomers or spindles) of the polyamine or polyamide type.

The combination according to the invention is advantageously characterized in that it comprises:
a first composition (A) comprising, in a medium which is suitable for topical application, at least one self-tanning active agent, preferably dihydroxyacetone, and
a second composition (B) comprising, in a medium which is suitable for topical application, at least one dendrimer.

The subject of the invention is also a device or kit comprising a first compartment comprising the abovementioned composition (A); a second compartment comprising the abovementioned composition (B), and a means of distribution which allows the sequential or simultaneous distribution of the two compositions.

Such two-compartment devices fitted with a suitable means of distribution are known per se, for example from the documents: WO 94/13258; WO 94/04130; WO 94/22419; FR-2,586,913, the disclosures of which are specifically incorporated by reference herein.

The subject of the invention is also a composition comprising, in a cosmetically acceptable medium, at least one self-tanning active agent, preferably dihydroxyacetone, and at least one dendrimer, as broadly defined above.

The self-tanning active agent, preferably dihydroxyacetone or DHA, is present in the compositions according to the invention in sufficient proportions to give the skin, when it is applied, a coloration similar to the coloration obtained following natural tanning. It is thus present in proportions preferably ranging from 0.1 to 20%, more preferably from 2 to 7%, by weight relative to the total weight of the composition, and even more preferably from 3 to 6% by weight relative to the total weight of the composition.

Advantageously, the dendrimer is present in proportions ranging from 0.01 to 20%, more preferably from 0.1 to 10%, by weight relative to the total weight of the composition.

A person skilled in the art will know how, by simple tests, to adapt the relative proportion of self-tanning active agent and of dendrimer in order to obtain the desired effect. Advantageously, in the combinations according to the invention, the proportion of self-tanning active agent, in particular of DHA, by weight relative to the weight of dendrimer preferably ranges from 1:10 to 10:1, more preferably from 1:5 to 5:1.

Among the standard cosmetic adjuvants which can be contained in the aqueous phase and/or in the silicone phase of the emulsions in accordance with the invention (depending on their water-soluble and/or liposoluble nature), mention may be made in particular of ionic or nonionic thickeners, softeners, antioxidants, opacifiers, stabilizers, emollients, insect repellants, organic sunscreens that are active in the UV-A and/or UV-B range, photoprotective inorganic pigments and nanopigments, moisturizers, vitamins, fragrances, preserving agents, fillers, sequestering agents, dyes or any other ingredients usually used in the field of self-tanning products.

Needless to say, a person skilled in the art will take care to choose this or these optional additional compounds and/or the amounts thereof such that the advantageous properties intrinsically associated with the composition in accordance with the invention are not, or are not substantially, adversely affected by the addition(s) envisaged.

The self-tanning compositions in accordance with the invention can be in the form of creams, milks, gels, cream gels, fluid lotions, in particular vaporizable fluid lotions, or any other form generally used in cosmetics, in particular a form which is usually suitable for self-tanning cosmetic compositions.

The subject of the invention is also a non-therapeutic treatment process for the skin, in order to give it a coloration close to that of natural tanning of the skin, this process being characterized in that an effective amount of at least one self-tanning active agent and of at least one dendrimer is applied to the skin, either in the same composition or separately over time. When the two components are applied in the same composition, this composition is preferably prepared just before use. If the two components are applied separately over time, it is preferably envisaged to apply the dendrimer first, followed, immediately or up to a few hours later, by the self-tanning active agent.

Another subject of the present invention is the use of the combinations as defined above, as, or for the manufacture of, cosmetic compositions for the artificial tanning and/or browning of the skin. As indicated above, the compositions can thus be conditioned in the form of creams, milks, cream gels or fluid lotions, in particular vaporizable fluid lotions, or any other appropriate form.

The subject of the invention is also a product containing at least one self-tanning active agent, and at least one polymer selected from dendrimers, as a combination product for simultaneous or separate use or for use spread out over time, for artificially tanning the skin.

The following tests illustrate the examples, but in no way limit it.

TESTS

All of the percentages indicated are given by weight of active material relative to the total weight of the composition.

Tests 1

The speed of appearance of the coloration obtained from successive applications on "Vitro-Skin™" (amount applied=2 mg/cm$^2$) of the following aqueous solutions:

110% DHA alone

10% DHA preceded by an application of 4% lysine solution

10% DHA preceded by an application of 4% polylysine solution

10% DHA preceded by an application of 4% dendrimer solution (STARBURST PAMAM from Dendritech, Generation 5)

10% DHA preceded by an application of 4% dendrimer solution (STARBURST PAMAM from Dendritech, Generation 1)

was compared by means of an "in vitro" test.

Measurements:

Colorimetric measurements (L*a*b system) with a Minolta CM-1000R colorimeter, as a function of the time before application (a$T_0$) and then at different time intervals;

Calculation of the overall colour change relative to $T_0$:

$$\Delta E = \sqrt{\Delta L^2 + \Delta a^2 + \Delta b^2}$$

Interpretation of the measurements: the higher the value of $\Delta E$, the greater the colour change.

Results:

The values of $\Delta E$ as a function of time for each of the tests and clearly show an acceleration in the colour change (thus the appearance of the artificial tanning) when DHA is combined with a dendrimer (STARBURST PAMAM from Dendritech, Generation 5 or STARBURST PAMAM from Dendritech, Generation 1). This acceleration was much greater than with a combination: DHA+amino acid (lysine) or DHA+polylysine.

Tests 2

The coloration obtained using the following cosmetic treatment procedures:

$P_1$—Application of an O/W emulsion prepared from the following constituents:

| | |
|---|---|
| Glyceryl stearate/OE fatty alcohols mixture | 3 g |
| Glyceryl stearate/OE polyethylene glycol stearate mixture | 2.5 g |
| Stearyl alcohol | 2.5 g |
| Silicone oils | 11 g |
| Oils (esters) | 6 g |
| Propylene glycol | 5 g |
| Dihydroxyacetone | 5 g |
| Preserving agents | qs |
| Water | qs 100 |

$P_2$—Application of a solution (2/1/1 ethanol/propylene glycol/water) containing 5% polyethyleneimine (POLYMIN G-35 sold by the company BASF) followed by application of the O/W emulsion according to $P_1$ $P_3$—Application of a solution (2/1/1 ethanol/propylene glycol/water) containing 5% dendrimer (STARBURST PAMAM of Generation 5, sold by the company Dendritech), followed by application of the O/W emulsion according to $P_1$ was compared by means of an "in vivo" test.

Evaluation Procedure:

The skin coloration obtained by applying the formulae described above was evaluated by means of an "in vivo" test on three volunteers:

Region tested: forearm, areas of 2.5×2.5 cm

Amount applied: 2 mg/cm$^2$

Monitoring of the colour change by colorimetry (Minolta CM-1000R):
before application ($T_0$)
24 h after the application ($T_{24\,h}$)

Results:

The results are expressed in the L*a*b colour space, in which:

The shade is expressed by the parameters a and b:
a represents the red-green axis (−a=green, +a=red)
b represents the yellow-blue axis (−b=blue, +b=yellow)

The $\Delta a/\Delta b$ ratio reflects the red/yellow equilibrium with:

$$\Delta a = a(T_{24\,h}) - a(T_0)$$

$$\Delta b = b(T_{24\,h}) - b(T_0)$$

given that the higher the value of $\Delta a/\Delta b$, the redder the shade of the coloration; a redder shade (i.e. a higher $\Delta a/\Delta b$ value) than that of DHA alone (too yellow) was desired.

The overall colour change relative to $T_0$ before application is represented by $\Delta E$:

$$\Delta E = \sqrt{\Delta L^2 + \Delta a^2 + \Delta b^2}$$

The results obtained in the evaluation of the shade and the evaluation of the overall colour are described in the following table:

| Procedure No. | Δa/Δb | ΔE |
|---|---|---|
| P$_1$ | 0.6 (+/−0.1) | 7.5 (+/−1.4) |
| P$_2$ | 0.4 (+/−0.1) | 4.9 (+/−1.7) |
| P$_3$ | 0.9 (+/−0.4) | 7.5 (+/−0.9) |

These results show that:
- relative to DHA alone, the combination with the dendrimer made it possible to obtain a less yellow shade (higher Δa/Δb) which is closer to that of a natural tan,
- relative to the combination DHA+polyethyleneimine, the combination DHA+dendrimer made it possible to obtain a greater colour change (stronger coloration intensity) and a less yellow, more balanced and thus more natural shade.

We claim:

1. A composition comprising at least one self-tanning active agent and at least one dendrimer wherein said at least one dendrimer is not a polyalkylamine.

2. A composition according to claim 1, wherein said at least one self-tanning active agent is selected from: mono- and polycarbonyl derivatives.

3. A composition according to claim 1, wherein said at least one self-tanning active agent is selected from dihydroxyacetone, isatin, alloxane, ninhydrin, glyceraldehyde, mesotartaric aldehyde and pyrazoline-4,5-dione derivatives.

4. A composition according to claim 3 wherein said at least one self-tanning active agent is dihydroxyacetone.

5. A composition according to claim 1, wherein said composition further comprises at least one compound selected from direct dyes and indole derivatives.

6. A composition according to claim 1, wherein said at least one dendrimer is selected from dendrimers containing amine terminal groups.

7. A composition according to claim 6, wherein said dendrimers containing amine terminal groups are selected from dendrimers in which the terminal groups bear a primary amine function.

8. A composition according to claim 6, wherein said dendrimers containing amine terminal groups are selected from polyamidoamines.

9. A composition according to claim 1, wherein said at least one dendrimer is selected from dendrimers containing base units selected from polyamines and polyamides.

10. A composition according to claim 1, wherein the proportion of said at least one self-tanning active agent by weight relative to the weight of said at least one dendrimer ranges from 1:10 to 10:1.

11. A composition according to claim 10, wherein the proportion of said at least one self-tanning active agent to said at least one dendrimer ranges from 1:5 to 5:1.

12. A method for producing a composition intended for at least one of artificial tanning or browning of the skin comprising including in said composition at least one self-tanning active agent and at least one dendrimer wherein said at least one dendrimer is not a polyalkylamine.

13. A cosmetic method for at least one of artificially tanning or browning skin comprising applying an effective amount to said skin of at least one self-tanning active agent and at least one dendrimer, wherein said at least one dendrimer is not a polyalkylamine, and further wherein said at least one self-tanning active agent and said at least one dendrimer are applied to said skin sequentially or simultaneously.

14. A cosmetic method according to claim 13, wherein said at least one self-tanning active agent and said at least one dendrimer are applied simultaneously as part of one composition prepared immediately before use.

15. A cosmetic method according to claim 13, wherein said at least one dendrimer is applied to said skin first, followed by application to said skin of at least one self-tanning active agent immediately or after a period of time.

16. An artificial tanning product comprising at least one self-tanning active agent and at least one dendrimer, wherein said at least one dendrimer is not a polyalkylamine.

* * * * *